United States Patent [19]

Goudy, Jr.

[11] Patent Number: 4,684,063
[45] Date of Patent: Aug. 4, 1987

[54] PARTICULATES GENERATION AND REMOVAL

[75] Inventor: Paul R. Goudy, Jr., Milwaukee, Wis.

[73] Assignee: Autotrol Corporation, Milwaukee, Wis.

[21] Appl. No.: 645,810

[22] Filed: Aug. 29, 1984

[51] Int. Cl.$^4$ .............................. B05B 5/00; B03C 3/04
[52] U.S. Cl. ............................................ 239/2.1; 55/5;
       55/107; 239/3; 239/8; 239/690; 239/14.1
[58] Field of Search ................... 239/2 R, 3, 8, 1, 690,
       239/2.1, 14.1; 55/107, 10, 5

[56] References Cited

U.S. PATENT DOCUMENTS

| 1,928,963 | 1/1925 | Chaffee | 239/2 R |
|---|---|---|---|
| 3,600,653 | 8/1971 | Hall | 55/5 |
| 3,630,441 | 12/1971 | Felici | 55/107 |
| 3,637,135 | 1/1972 | Luderer et al. | 239/3 |
| 4,190,875 | 2/1980 | Smart et al. | 55/107 |

FOREIGN PATENT DOCUMENTS 623583  8/1978  U.S.S.R. .................................. 55/5

*Primary Examiner*—Andres Kashnikow
*Attorney, Agent, or Firm*—Renner, Otto, Boisselle & Lyon

[57] ABSTRACT

A mixer/charger is used simultaneously to mix and electrically to charge a fluid or fluid-like material, and such electrically charged product is distributed into another fluid for various purposes. In one case the charged product may be mixed with particulate matter used to form smoke—an apppropriate polarity can cause repulsion of the smoke producing particulates thereby to reduce agglomeration and to maximize the suspension time of such particulates in surrounding environment. Alternatively, by distributing the charged product into particulate containing fluid and selecting the polarity such that such particulates tend to agglomerate, expeditious removal of such particulates can be accomplished. The charged product also may be used for distributing mist, distributing ionic material in air, e.g. for sense of wellbeing, and for seeding clouds.

29 Claims, 15 Drawing Figures

PARTICULATES GENERATION AND REMOVAL

TECHNICAL FIELD

The present invention relates generally, as indicated, to the generation and removal of particulates and, more particularly, to the use of an electrically charged product in apparatus and method for generating charged material, generating and suspending particulates in a suspending fluid, and for removing particulates from a suspending fluid.

CROSS REFERENCE TO RELATED APPLICATIONS

Reference is made to copending, commonly assigned, concurrently filed, U.S. patent applications Ser. No. 645,809 for "Fluid Mixer/Charger and Method" and Ser. No. 645,841 for "Charged Fluid Reaction Control", the entire disclosures of which hereby are incorporated by reference.

BACKGROUND OF THE INVENTION

Reference also is made to issued U.S. Pat. Nos. 4,259,021 and 4,329,067, which disclose motionless mixers for fluids, and the entire disclosures of such patents also hereby are incorporated by reference.

One difficulty in making smoke for distribution in an air environment is the uniformity of distribution of the smoke producing particulates and the longevity of suspension of the smoke producing particulates in the air environment. It would be desirable to facilitate uniformity of such distribution and to increase the duration of suspension.

In environments where smoke particulates or other particulates or fluid-like material is contained in another suspending material, such as air, difficulty often is encountered in removing the same from such suspending material. For example, in the case of smoke contained in air, if one were simply to blow fresh air into the smoky area, turbulence may be encountered, but absolute dissipation of the smoke particulates often is not expeditiously achieved. Accordingly, it would be desirable to facilitate and to expedite the removal of such particulates, etc., from another suspending fluid, such as air.

Moreover, it would be desirable to accomplish the foregoing and the various other advantages and features of the invention, as will become more apparent from the description below, using relatively low power requirements.

It is well known that the use of charged particles, such as ionized air, etc., in a local environment can contribute to a general sense of well being to people inhabiting the particular area or environment.

Moreover, a problem encountered in seeding clouds for producing rain is the too rapid dissipation of the seeding material. It would be desirable to maximize seeding while also minimizing the cost, energy, and time to effect seeding.

SUMMARY OF THE INVENTION

In accordance with the present invention, a mixer/charger of the type disclosed in the first-mentioned patent application above is employed simultaneously to mix and to electrically charge a fluid flowing therethrough, and the charged fluid product is used for a variety of purposes. Such purposes will become more apparent from the detailed description below.

One aspect of the invention relates to apparatus for generating a relatively long term suspension of a first particulate/first fluid material in a suspension fluid, comprising fluid mixer/charger means for mixing and electrically charging a second fluid, and distributing means for distributing such charged second fluid and such particulate/first fluid material in such suspending fluid.

Another aspect relates to a method for generating smoke, comprising electrically charging air at a polarity that is the same as the usual polarity of smoke producing particulate material, mixing such electrically charged air and such smoke producing particulate material, and distributing such mixture to external environmental air.

A further aspect relates to a method for increasing the time that particulate or like material remains suspended in another suspending material, comprising charging a first fluid at a polarity that is the same as the natural electrical polarity of such particulate material, mixing such charged first fluid with such particulate material, and distributing such mixture into such suspending fluid.

Yet another aspect relates to apparatus for removing particulates/first fluid material from a suspending fluid in which such particulate/fluid material is suspended, comprising mixer/charger means for simultaneously mixing and electrically charging a second fluid, and distributing means for distributing such charged second fluid into such suspending fluid to cause agglomeration of such particulate/first fluid material causing the same to tend to separate from such suspension fluid.

Yet an additional aspect relates to a method of removing particulate/first fluid material from a suspending fluid, comprising simultaneously mixing and electrically charging a second fluid at a polarity opposite that at which such particulate/first fluid material ordinarily is charged, and distributing such charged second fluid into such suspending fluid to charge such particulate/first fluid material, whereby such particulate/first fluid material tend to agglomerate and to separate from such suspending fluid.

Yet a further aspect relates to a method of seeding clouds, comprising forming a mist including water, mixing and electrically charging at least one of a supply of water and such mist, and distributing such charged mist to effect seeding.

Even another aspect relates to a method of charging air, comprising directing air through a mixer/charger, simultaneously mixing and electrically charging such air flowing through the mixer/charger, and distributing the air into the surrounding environment.

These and other objects and advantages of the present invention will become more apparent as the following description proceeds.

To the accomplishment of the foregoing and related ends, the invention, then comprises the features hereinafter fully described in the specification and particularly pointed out in the claims, the following description and the annexed drawings setting forth in detail a certain illustrative embodiment of the invention, this being indicative, however, of but one of the various ways in which the principles of the invention may be employed.

DESCRIPTION OF THE PREFERRED EMBODIMENT

Figure 1:
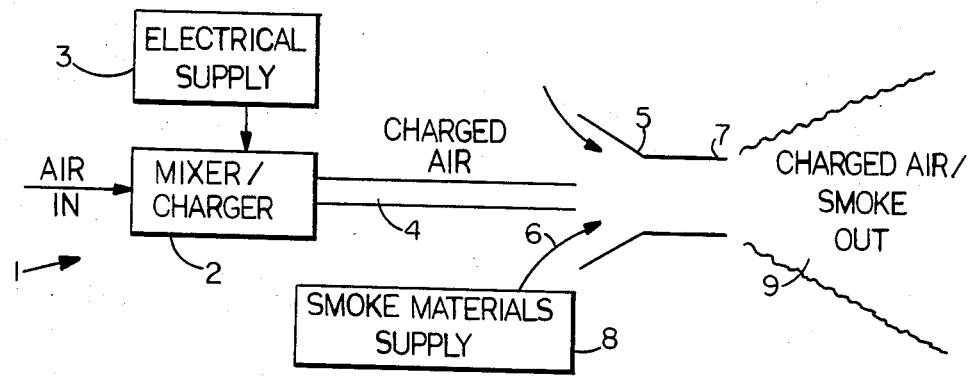
FIGS. 1 and 2 are schematic block diagram illustrations of a mixer/charger apparatus and method for producing smoke.

Referring in detail to the drawings, wherein like parts are designated by like reference numerals in the several figures, and initially to FIG. 1, a smoke generating system 1 in accordance with the present invention is illustrated. The system 1 includes a mixer/charger 2 of the type disclosed in the first mentioned application above. A more comprehensive description of the mixer/charger 2 excerpted from the first mentioned application above is presented near the end of this specification with references to FIGS. 10–15. Such mixer/charger may include, for example, an inlet for receiving an input flowing fluid, the inlet including a flow directing mechanism for directing fluid in a first directional flow path, an outlet positioned to receive fluid flowing from the inlet to direct that fluid along a second directional flow path different from the first, a mechanism for thoroughly mixing the fluids by dividing and recombining fluid streams and effecting turbulent mixing of the fluid, and an electrical charging arrangement of a capacitive type to apply or to remove electrical charge with respect to fluid during flow through the device. An electrical supply 3 provides electrical input to the mixer/charger, which preferably is a motionless mixer type device. An air input is provided the mixer/charger, and charged air 4 is produced at the output of the mixer/charger. The charged air 4 is delivered to a combiner type fluid mixer 5, for example of a Venturi type in which the charged air 4 is delivered to the center of such device, and additional material following the direction of the arrows 6 is mixed with the charged air and is delivered to the output 7 of the combiner/mixer 5. In the preferred embodiment illustrated in FIG. 1, the materials following the direction of the arrows 6 are smoke producing particulate materials from a smoke materials supply 8. The resulting product produced by the apparatus 1 in the form of a charged air/smoke output 9 is delivered to the external ambient environment of the apparatus, as is seen in FIG. 1.

According to operation of the invention, to maximize the duration that the smoke producing particulate materials from the supply 8 are held in suspension in the air at the location 9 and preferably also to improve the overall distribution and preferably uniformity of distribution, of such smoke in the environment 9, the mixer/charger 1 charges the air of a polarity such that the charged air 4 is at the same polarity as the normal polarity of the smoke producing materials themselves. Accordingly, the actual electrical charge of such smoke producing materials is increased to the extent that such materials tend to repel each other and agglomeration thereof is minimized. Therefore, such materials tend to remain suspended in the ambient environment 9 for a longer period of time than would particles that otherwise would agglomerate relatively rapidly, would increase in weight, and would tend to drop out of the environment under the force of gravity.

Accordingly, the apparatus 1 may be used to produce smoke or to produce another particulate material that is distributed in the ambient environment for a relatively long period of time by producing a charged fluid at the output 4 from the mixer/charger of a polarity that is the same as the polarity of the particulate material intended for suspension. The charged product at the output 4 is mixed with the other particulates or even a further fluid material produced by such a supply as that shown at reference numeral 8, and the combination is then distributed to the environment 9, which may be air or other environment.

Figure 2:
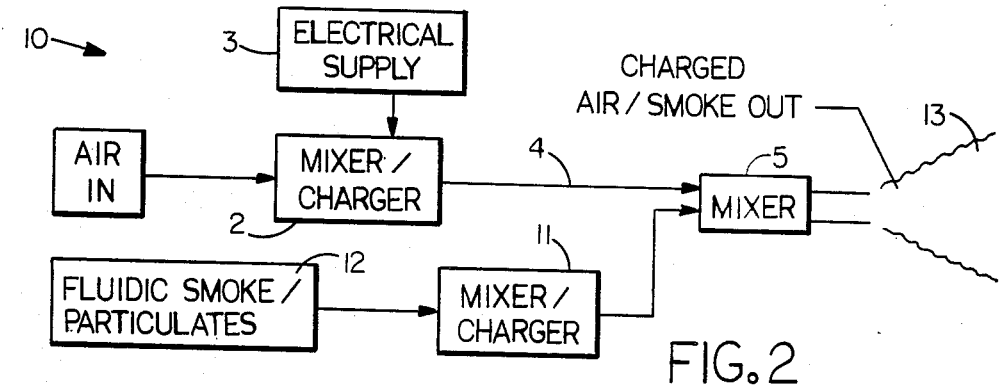

Turning briefly to FIG. 2, a modified apparatus 10 for producing a charged air/smoke output is illustrated. The apparatus 10 includes a mixer/charger 2, electrical supply 3, and a combiner/mixer 5, as above. Such combiner/mixer combines charges air 4 at the output of the mixer/charger 2 with also charged fluidic smoke/particulates produced by a further mixer/charger 11. Such further mixer/charger 11 may be the same type of device as mixer/charger 2; however, the mixer/charger 11 effects application of an electrical charge to fluidic materials, smoke producing particulates, etc., supplied from a source 12. The polarity of the product produced by the mixer/charger 11 and the polarity of the product produced by the mixer/charger 2 preferably should be the same so that after the two products are combined in the mixer 5, substantial repulsion due to like charges of the various particulates will occur in the output 13. Such output may include such charged mixture which may be distributed in the external environment of the apparatus 10 for suspension for a relatively long period of time.

Figure 3:
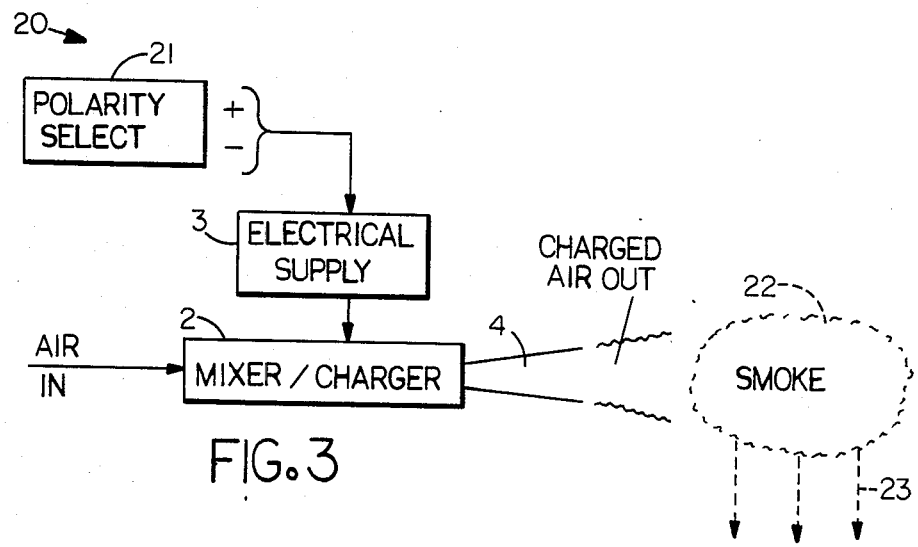
FIG. 3 is a schematic block diagram illustration of the invention used to remove smoke from air.

Referring to FIG. 3, now, an apparatus 20 for removing smoke or other particulates from another fluid, such as air, is illustrated. The apparatus 20 includes a mixer/charger 2, an electrical supply 3, and a polarity select switch 21. The mixer/charger 2 produces a charged air output 4, which is delivered into the environment 22 in which smoke particulates are contained. The polarity select switch 21 determines the polarity of charge applied to the air 4. Such polarity is selected to be different from the natural polarity of the smoke producing particulates in the environment 22. Such charged air tends to mix with the particulates tending to cause the same to agglomerate and to drop out of the ambient environment, as is represented by the arrows 23 in FIG. 3.

Figure 4:
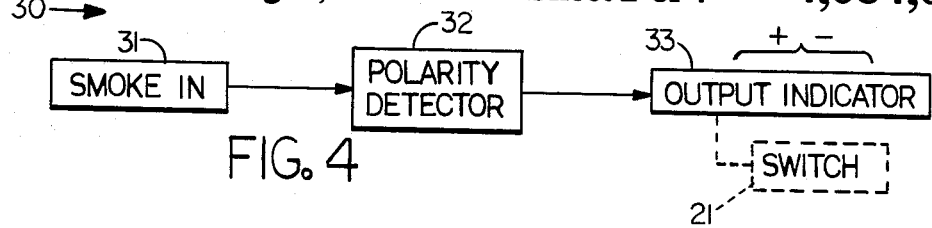
FIG. 4 is a schematic block diagram illustration of a polarity detector useful to determine polarity of particulate matter in conjunction with the invention.

To assure application of the proper polarity electrical charge to the air 4 in the output of the apparatus 20 illustrated in FIG. 3, a polarity detector may be used. Such a polarity detector is shown in FIG. 4 at reference numeral 30. The polarity detector apparatus 30 has an input 31 for receiving smoke taken as a sample for the environment 22 (FIG. 3), a polarity detector of conventional design, such as a charge detecting device with appropriate electrodes, circuitry and meter equipment, generally of conventional design and represented schematically at 32, and an output indicator 33 for indicating the charge polarity of the smoke 31. The indicator 33 may be coupled to the polarity select switch 21 (FIGS. 3 and 4) for automatic selection of the polarity of the electrical supply 3 and determination of the polarity of the charging of the air 4 in the apparatus 20 (FIG. 3). Alternatively, the output indicator 33 may provide a visual or other output indication of the detected polarity of the smoke 31, and that information may be used manually or otherwise to select the polarity of the electrical supply 3 according to the polarity select switch 21 (FIG. 3).

Figure 5:
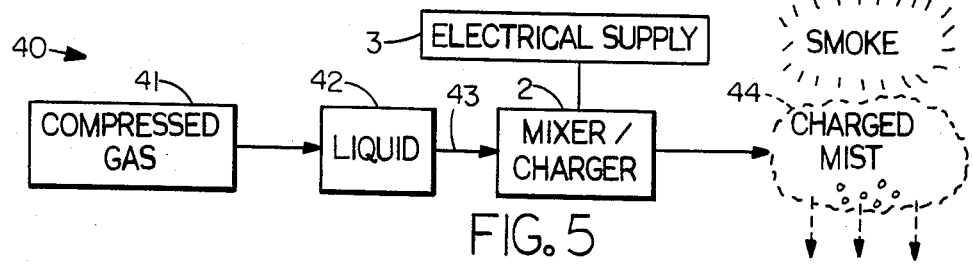
FIGS. 5 and 6 are schematic block diagram illustrations of two different embodiments of the invention used to produce a charged mist.

Another alternate embodiment of apparatus 40 for removing smoke from a particular environment is illustrated in FIG. 5. The apparatus 40 generates a charged mist which may be distributed into the smoke containing environment to effect agglomeration of the smoke particulate materials and, accordingly, the settling of those materials out from the environment according to the force of gravity. The apparatus 40 includes a source of compressed gas 41 that is coupled to a liquid supply 42 to produce a mist-like output at 43. The mist 43 is provided as an input to a mixer/charger 2 to which an electrical supply 3 is coupled. The mixer/charger 2 effects charging of the mist to produce a charged mist output 44. The charged mist output is directed into the smoke containing environment, tends to effect charging of the smoke and wetting of the smoke to effect agglomeration and settling out of the smoke producing particulates under the influence of gravity, thereby tending to cleanse the environment of the smoke in a relatively efficient and rapid manner. It will be noted that the charged mist also can be used for other purposes. An example might be to provide a relatively uniformly distributed moist environment to contain or to resist combustion, otherwise to humidify air, etc.

Figure 6:
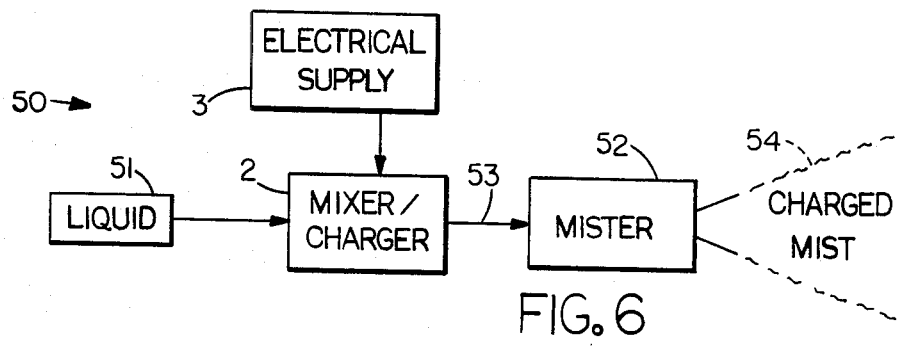

In FIG. 6 an apparatus 50 to produce a charged mist output is shown. The apparatus 50 includes a supply of liquid 51, a mixer/charger 2, electrical supply 3, and a mister 52. The mixer/charger 2 effects charging of the liquid from the supply 51 to produce a charged liquid output at 53. The mister 52 may be, for example, a conventional humidifying type device including a spinning wheel, brush, or the like, that flings the liquid or small portions thereof, into the surrounding environment to produce a charged mist output at 54. The charged mist may be used, for example, for the various purposes mentioned above. The mister 52 may be another type of device capable of creating from the liquid input thereto a mist output.

Figure 7:
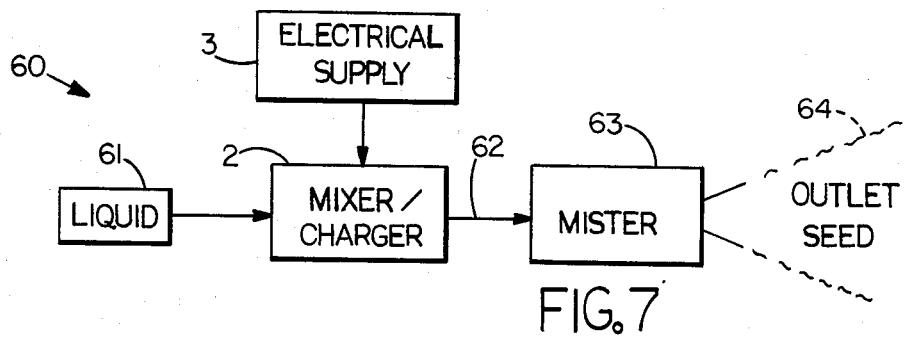
FIGS. 7 and 8 are schematic block diagram illustrations of two embodiments of the invention used to produce material for seeding clouds.
Figure 8:
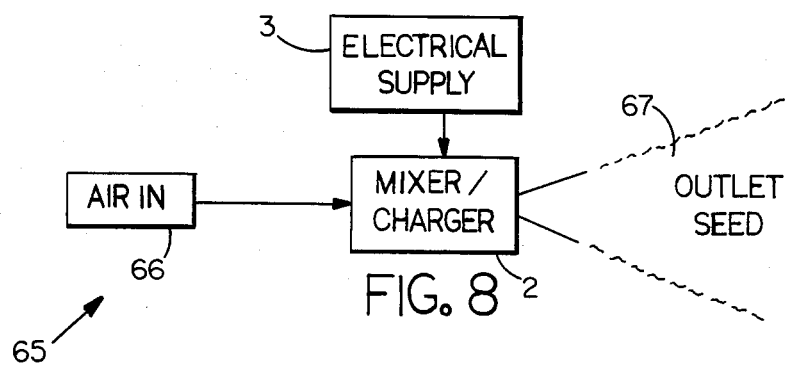

According to the invention, the charged output produced thereby may be used for seeding clouds for the usual purposes. In FIG. 7 an apparatus 60 for effecting such seeding is illustrated. The apparatus 60 includes a liquid supply 61, for example of water or other fluid from which the charged mist ultimately is produced to effect seeding. The apparatus 60 also includes a mixer/charger 2 and an electrical supply 3 which effect production of a charged fluid output 62 that is delivered to a conventional mister 63, for example of the type described above in FIG. 6 with respect to the mister 52. The mister 63 produces a charged mist output 64 used to effect seeding. Due to the charged nature of the output 64, the same tends to provide both electrical and other physical attraction of, for example, water vapor, to effect development of clouds and/or a subsequent rain. In FIG. 8 is an alternate version of apparatus 65 used to effect seeding. The apparatus 65 employs an air input supply 66 that is delivered to a mixer/charger 2, which receives an electrical input from the electrical supply 3. The apparatus 65 produces a charged air output 67 used to effect seeding function as was described above with respect to the apparatus 60.

Figure 9:
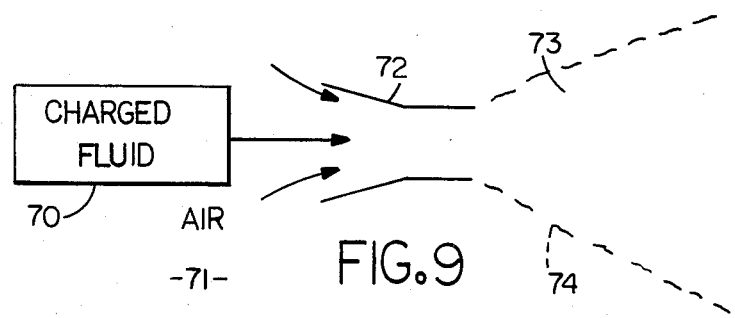
FIG. 9 is a schematic block diagram illustration of the invention used to produce charged air for achieving a sense of well being in a local environment.

The mixer/charger 2 according to the invention also may be employed to produce a charged fluid represented at 70 in FIG. 9. Such charged fluid then may be combined with air represented at 71 in a Venturi type or other type of fluid combining device 72 to produce a charged air output 73 distributed into a local environment represented at 74. Such charged air environment may be used to effect a sense of well being by persons located therein.

Referring to FIGS. 10–15, a mixer/charger device in accordance with the preferred embodiment and best mode of the present invention is generally indicated at 200. The mixer/charger 200 includes a fluid inlet 111 for receiving a flow of fluid from an external source, a plurality of disc-like or plate-like members 112, 113 each being generally fluid impermeable and each having one or more fluid passing openings therethrougn, such as those shown at 114, 115, a holder mechanism generally indicated at 116 for holding the discs 112, 113 in relative position for directing the flow of fluid through the device 2 (the discs and holder mechanism preferably forming an overall fluid flow path through container 117), and a fluid outlet 118 for directing or coupling fluid from the mixer/charger device 200 as a fluid output therefrom. Preferably the discs 112, 113 are electrically conductive, for example being formed of copper, aluminum or other electrically conductive material, and electrical leads 120, 121 couple such discs to a source of electric energy or electric power 122, for example such as a DC battery, a DC power supply, or any other electrical supply, as may be desired to apply an electric potential across a pair of discs 112, 113 to supply a source of electrons or to remove electrons with respect to fluid flowing through the mixer/charger device.

The holder mechanism 116 includes a retainer ring 123 preferably of electrically nonconductive material, which suports the disc 112; an insulator ring/cover 124, which holds the disc 113 and also provides electrical insulation for preferably the entire disc, and a fastener 125, such as a bolt, nut, washer, etc. assembly for example of the type illustrated. It is the purpose of the holder mechanism 116 to cooperate with the discs 112, 113 and with the fluid inlet 111 and fluid outlet 118 to form the container 117 that preferably has substantial fluid-tight integrity to prevent leakage of fluid therefrom while fluid is permitted to flow from the fluid inlet to the fluid outlet. As is described in greater detail below, it is preferable that the flow of fluid through the mixer/charger 200 be substantially unimpeded, although the direction of fluid flow may vary in the device and although the fluid flow may be divided into multiple streams and recombined into a fewer or into one single stream during flow through the mixer/charger 200. By minimizing flow impedance in the mixer/charger 200 dead spots, i.e. spots where fluid tends to stagnate in the device while fluid flows at other portions, and boundary layer formation, both of which would tend to reduce the mixing effectiveness and/or charging effectiveness of the mixer/charger 200 preferably are minimized.

Figure 10:
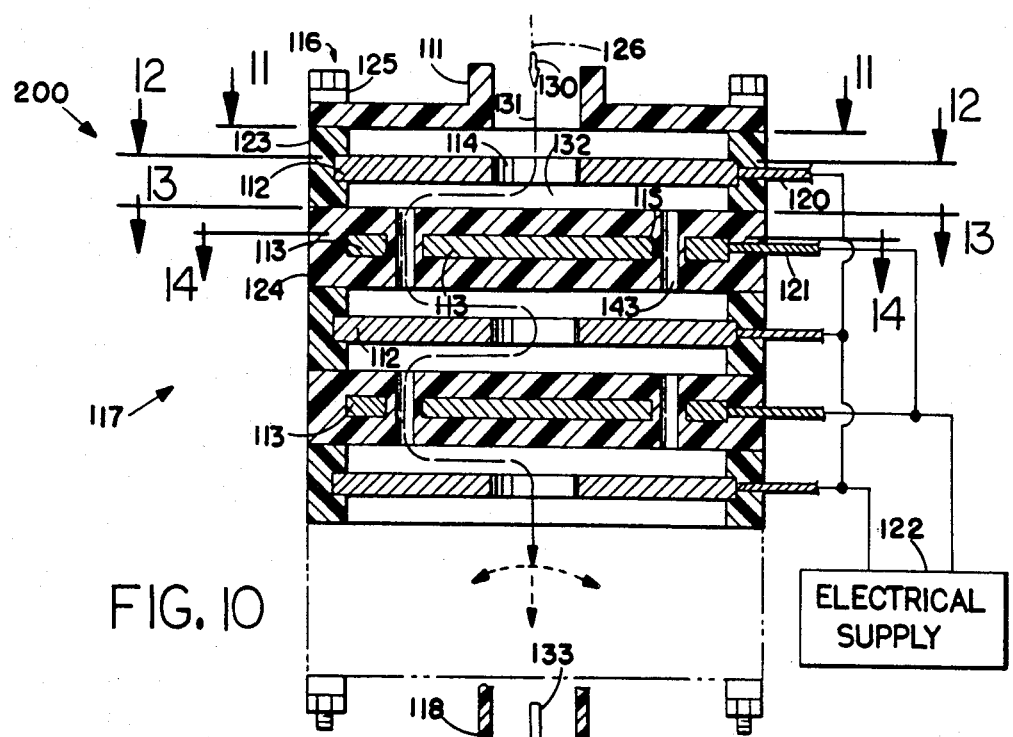
FIG. 10 is an elevation view, partly in section, of a mixer/charger device used in the present invention.
Figure 11:
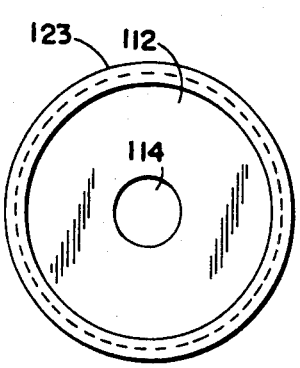
FIGS. 11, 12, 13, and 14 are respective plan views, some partly in section, looking generally in the direction of the respective section lines shown in FIG. 10.
Figure 12:
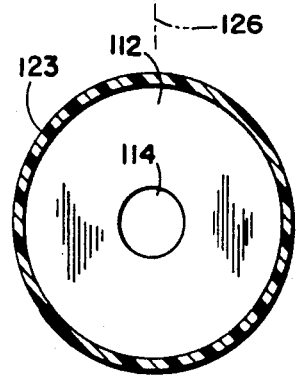
Figure 13:
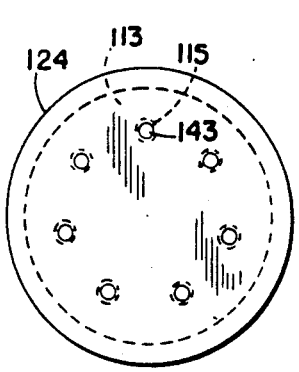
Figure 14:
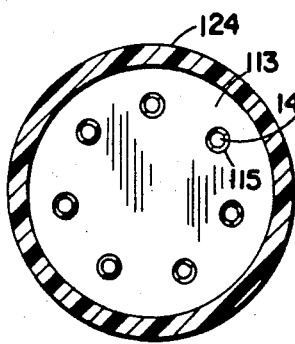

According to fluid flow operation of the mixer/charger 200 an upstream one of the discs 112, 113 provides or serves as an inlet to the next downstream disc. Moreover, one of a pair of discs 112, 113 has a different number of openings therethrough than the other of the discs 112, 113 so that as fluid flows through one disc and then through the next downstream disc, the number of streams of which the overall fluid flow is composed changes. In the illustration of FIG. 10, the most upstream disc 112 has a single opening therethrough and the next downstream disc 113 has a plurality of openings therethrough. Moreover, to minimize impeding fluid flow through the mixer/charger 200 to avoid dead spots, and to avoid boundary layer formation and detriment vis-a-vis application of charge to fluid flowing through the mixer/charger, the approximate total area of the single opening and the sum of the total areas of the multiple openings in each of the discs are the same. Reference to area here is intended to mean the approximate area across an opening or the sum of the areas across each of the openings through a multiple opening disc, such area being taken approximately in a plane that is normal to the general direction of flow of fluid through such opening.

Further, it is preferred that the openings in respective relatively adjacent discs, such as the pair of discs 112, 113 that immediately follow each other in the mixer/charger 200 of FIG. 10, have respective openings that are relatively offset from each other. Accordingly, the opening 114 in the disc 112 seen in FIG. 10 is approximately at the center of the disc 112 generally along the linear flow axis 126 drawn longitudinally through the mixer/charger 2; and the openings 115 through the disc 113 are at a different radial location relative to the axis 126 offset from the same. Such offset or staggered relationship of the openings 114, 115 enables the openings themselves and the plates in which they are formed to effect a change in the directional flow of the fluid through the mixer/charger preferably also as the number of streams in which the fluid flows changes from plate to plate.

Accordingly, during the flow of fluid through the mixer/charger of FIG. 10, an input supply of fluid is provided at 130 from a supply (not shown), and such fluid flows through the fluid inlet 111. The fluid follows along a flow path represented by the line 131 through the opening 114 in the disc 112. On flowing through the opening 114, the fluid flow changes direction from one generally parallel to the axis 126 to one generally normal to the axis 126. Moreover, during the course of such change in direction, a turbulent mixing of fluid occurs at the area 132. The flow stream then changes direction again to one of the openings 115 in the next downstream disc 113; the fluid passes through such opening 115 and again changes direction as it encounters the impermeable surface of the next downstream disc 112 and then flows toward the opening 114 therein encountering further mixing. Thus, fluid flow along the path 131 results in the dividing and recombining of flow streams, turbulent mixing, and directional changes of fluid flow, all of which cooperate to ensure a highly effective mixing of the fluid. Ultimately, the fluid exits the fluid outlet 118 as an exit flow 133 for subsequent use downstream of the mixer/charger 200.

The arrangement of the retainer ring 123 and insulator ring/cover 124 (FIG. 10) provides the functions of holding the respective discs 112, 113 in appropriate positions in the mixer/charger 200 for effecting the desired fluid flow, mixing and charging functions and preferably also of completing the fluid-tight integrity of the mixer/charger 200 forming the container 117.

To effect application of electrons to fluid flowing through the mixer/charger 200 or to remove electrons from such fluid, electrical power is provided from the supply 122 across respective pairs of discs 112, 113. Thus, for example, an electric potential may be connected via leads 20, 21 to one or more pairs of relatively adjacent discs 112, 113, as is seen in FIG. 10, for example. Application of charge to a fluid flowing through a mixer/charger 200 according to the invention was achieved using a voltage applied across a pair of relatively adjacent discs 112, 113 in the range of from greater than 0 to approximately 25,000 volts with a current flow in the milliamp range. Satisfactory charging of air flowing through the mixer/charger device 2 at a rate of approximately ½ cubic foot per minute was accomplished using such electrical energy levels. Such charging may be the application of electrons to the air, for example by providing a source of electrons or supply of electrons to the disc 112 while the insulated disc 113 is maintained at a relatively lower electric potential. Alternatively, the polarity could be reversed whereby a supply of electrons would be provided the insulated disc 113 while the disc 112 was at a relatively lower electric potential; in this case electrons essentially are removed from the fluid. Thus, according to the invention, reference to charging of fluid may refer equivalently to the application of electrons or the removal of electrons with respect to the fluid.

The mixer/charger 200 functions in a sense as a capacitor whereby the relatively adjacent discs 112, 113, for example, form the opposite plates of the capacitor, and the dielectric constant of the capacitor may be a function of the dielectric constant of the insulator ring/cover 124 and the dielectric constant of the fluid between adjacent discs. Thus, if the fluid were air, the mixer/charger 200 would function like an air capacitor. Such capacitor according to the invention, then, is provided with a controlled bleed of electric charge, and such bleed may be a function of the aforementioned dielectric constant values, of the usual parameters, such as capacitor plate size, temperature, voltage and/or current values, etc., and such controlled bleed may also be a function of the flow rate of fluid through the mixer/charger 200. The flow rate and/or mixing may alter the effective distribution of charge in the fluid, the wiping or scrubbing action of the fluid against respective discs and/or the insulator ring/cover 124 surface(s), etc. As the fluid mixes during flow, charge tends to be distributed through the fluid thereby helping to maximize the overall charging as the fluid flows across and through respective discs. As the area of the openings 114 and the sum of the areas of the openings 115 in respective discs is approximately the same, dead spots and boundary layers will be minimized and preferably avoided in total so as to maximize the continuing flow of fluid through the mixer/charger, distribution of charge in the fluid, wiping action of the fluid against respective discs, etc.

It is noted here that although reference to wiping of a disc, such as disc 113, may be stated herein, in the event such disc is protected by an insulator ring/cover 124, for example as is shown in FIG. 10, such referral indicates wiping action against the exposed surface area of the insulator ring/cover 124. In any event, as the fluid wipes across or scrubs over respective discs, charge is transferred or removed with respect to the fluid, i.e. electrons are added or removed with respect to the fluid. Additionally, since there is a relatively large surface area available in the mixer/charger 200 for such charge transfer, a greater concentration of charge and transfer thereof to fluid flowing through the mixer/charger can be accomplished than was heretofore possible in prior art devices.

After a fluid has been charged in the mixer/charger 200 it may be desirable to maintain such charge for a maximum period of time. For such purposes, it is desirable that the fluid outlet 118 be of an electrically nonconductive material that tends not to dissipate, to bleed, to ground, or otherwise to affect the charge of the fluid 133 as the same passes through the fluid outlet 118. It also may be desired to form the fluid inlet 111 of material similar to that of which the fluid outlet 118 is made in order to avoid pre-charging or pre-affecting the charge of the fluid input 130; alternatively, in order to help neutralize any pre-existing charge on the input fluid 130, it may be desired to select the fluid inlet 111 to be of a material that is electrically conductive and does in fact tend to neutralize pre-existing charge. Furthermore, if desired, the container 117 may include an additional housing (not shown) surrounding those portions of the mixer/charger 200 illustrated in FIG. 10 for further fluid-tight integrity thereof, electrical isolation thereof, thermal insulation thereof, etc.

Figure 15:
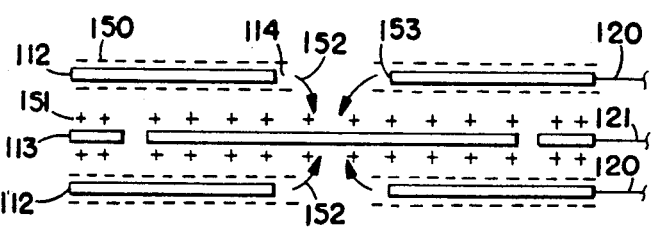
FIG. 15 is a schematic illustration of charge distribution and flow in a mixer/charger device according to the invention.

Turning now to FIG. 15, three representative discs 112, 113 are illustrated coupled by respective leads 120, 121 to an electrical supply. The discs 112 are shown having a source or excess supply of electrons (represented by minus signs) and the disc 113 is shown having a dearth of electrons, i.e. being at a relatively lower relative electric potential (with representation thereof being shown by the plus signs 151 on both sides thereof). Arrows 152 represent the tendency of electrons to flow from the source thereof toward the source of relatively lower electric potential. Due to such tendency of electron flow represented by arrows 152, the edge 153 circumscribing the center opening 114 in each disc 112 tends to become an area of rather high electrical stress, this in particular when the discs 112 have the source of electrons. (Such discs 112 may be considered electrically, i.e. in conventional electrical engineering terms as the positive plate and the disc 113 may be considered the ground plate or relatively negative plate in such circumstances, according to ordinary convention.)

Applicant has discovered that a mixer/charger according to the present invention may have an optimum length and an optimum number of discs 112, 113 forming respective capacitors therein. Too long a mixer/charger and, accordingly, flow path with too many such plates may result in inefficiency and in some instances may result in a loss of charge of the fluid after a maximum charge already had been developed. Thus, it may be necessary to use a pragmatic approach to determine an optimum length for an optimum fluid to effect the desired charging without discharging the fluid.

In using the mixer/charger of the invention, then, it will be appreciated that a fluid is provided to the mixer/charger. The mixer/charger thoroughly mixes the fluid by changing the number of streams in which the fluid is flowing from one or a relatively few streams to a relatively larger number of streams while also changing the flow direction of the various streams and enabling a relatively turbulent mixing of the fluid between and at respective discs. Simultaneously electric charge is applied or removed with respect to the fluid flowing through the mixer/charger.

The discs may be plate-like, fluted, truncated conical, etc. and preferably are of electrically conductive material, such as copper, aluminum, steel, or the like, preferably being impermeable to fluid flow other than at the distinct openings therethrough. The retaining ring 123 and insulator ring/cover 124 preferably are of electrically nonconductive material as also preferably is the fluid inlet 111 and fluid outlet 118.

The apparatus and methods of the invention may be used with particulates other than smoke and with fluids other than air or water. Examples of other particulates may be dust, biological materials, noxious materials, etc.

STATEMENT OF INDUSTRIAL APPLICATION

According to the invention, then, a charged fluid product may be used for the variety of purposes discussed above.

I claim:

1. Apparatus for generating a relatively long term suspension of a first particulate/first fluid material in a suspension fluid, comprising fluid mixer/charger means for simultaneously thoroughly mixing and electrically charging a second fluid, and distributing means for distributing such charged second fluid and such particulate/first fluid material in such suspending fluid, said mixer/charger means comprising inlet means for receiving an input flowing fluid, outlet means positioned to receive fluid from said inlet means for directing an output flowing fluid, said inlet and outlet means including cooperative means for dividing at least one stream of fluid into plural streams and for at least once changing at least one of the relative flow direction and relative location of at least part of one of such streams, and charge coupling means for coupling or removing an electrical charge with respect to at least one of said inlet means and outlet means to affect the charge of fluid flowing in the device.

2. The apparatus of claim 1, said mixer/charger means comprising mixer/charger means for electrically charging such particulate/first fluid material at an electrical polarity that is the same as the normal electrical polarity charge thereof tending to cause the same to repel and to minimize agglomeration.

3. The apparatus of claim 2, said second fluid comprising air.

4. The apparatus of claim 3, said particulate/first fluid material comprising smoke producing particulate material.

5. The apparatus of claim 1, further comprising combining means for combining such particulate/first fluid material with said second fluid material downstream of said mixer/charger means.

6. The apparatus of claim 5, said second fluid comprising air and said particulate/first fluid material comprising smoke producing material, and said combining means comprising a fluidic combiner.

7. The apparatus of claim 5, further comprising further mixer/charger means for mixing and electrically charging said particulate/first fluid material, and said further mixer/charger means and first mentioned mixer/charger means being coupled to provide a fluidic input to said combining means, and the output of said combining means being coupled to provide an input to said distributing means.

8. The apparatus of claim 1, further comprising an electrical supply means for providing electrical energy to said mixer/charger means for effecting such electrical charging function.

9. The apparatus of claim 1, said inlet means including directing means for directing fluid in a first directional flow path, said outlet means being positioned to receive fluid flowing from said inlet means for directing such fluid along a second directional flow path different from such first directional flow path, and charging means for applying or removing electrical charge with respect to fluid during flow by at least one of said inlet and outlet means.

10. The apparatus of claim 1, wherein said particulate/first fluid material comprises biological material and said second fluid material comprises air.

11. A method for generating smoke, comprising electrically charging air at a polarity that is the same as the usual polarity of smoke-producing particulate material, electrically charging such smoke-producing particulate material, mixing such electrically charged air and electrically charged smoke-producing particulate material, and distributing such mixture to external environmental air.

12. The method of claim 11, said electrical charging further comprising simultaneously mixing and electrically charging such air.

13. A method for increasing the time that particulate or like material remains suspended in another suspending material, comprising charging a first fluid at a polarity that is the same as the natural electrical polarity of such particulate material, mixing such charged first fluid with such particulate material, and distributing such mixture into such suspending fluid.

14. The method of claim 13, wherein said suspending fluid comprises air.

15. The method of claim 14, said first fluid comprising air.

16. The method of claim 15, said particulate material comprising smoke producing particulate material, whereby upon distributing such mixture into air, smoke is generated.

17. The method of claim 16, further comprising electrically charging such smoke particulate material prior to mixing with such charged air.

18. Apparatus for removing particulates/first fluid material from a suspending fluid in which such particulate/fluid material is suspended, comprising mixer/charger means for simultaneously mixing and electrically charging a second fluid, and distributing means for distributing such charged second fluid into such suspending fluid to cause agglomeration of such particulate/first fluid material causing the same to tend to separate from such suspension fluid, said mixer/charger means comprising inlet means for receiving an input flowing fluid, outlet means positioned to receive fluid from said inlet means for directing an output flowing fluid, said inlet and outlet means including cooperative means for dividing at least one stream of fluid into plural streams and for at least once changing at least one of the relative flow direction and relative location of at least part of one of such streams, and charge coupling means for coupling or removing an electrical charge with respect to at least one of said inlet means and outlet means to affect the charge of fluid flowing in the device.

19. The apparatus of claim 18, said inlet means including directing means for directing fluid in a first directional flow path, said outlet means being positioned to receive fluid flowing from said inlet means for directing such fluid along a second directional flow path different from such first directional flow path, and charging means for applying or removing electrical charge with respect to fluid during flow by at least one of said inlet and outlet means.

20. The apparatus of claim 18, further comprising a supply of air for delivery to said mixer/charger means as said second fluid.

21. The apparatus of claim 20, said mixer/charger means comprising means for electrically charging said second fluid to a polarity opposite to that normally occuring in such particulate/first fluid material.

22. The apparatus of claim 18, further comprising misting means for generating an electrically charged mist.

23. The apparatus of claim 22, said misting means comprising means for mixing water and air for delivery to said mixer/charger means for electrical charging therein.

24. The apparatus of claim 22, said misting means comprising means for generating a mist of water and such electrically charged air produced by said mixer/charger means.

25. The apparatus of claim 18, further comprising polarity sensor means for sensing the polarity of such particulate/first fluid material.

26. The apparatus of claim 25, further comprising switch means for setting the polarity at which said mixer/charger means charges such second fluid.

27. The apparatus of claim 18, said particulate/first fluid material comprising smoke producing particulate material, and said suspending fluid comprising air.

28. The apparatus of claim 18, said particulate/first fluid material comprising biological material.

29. A method of electrically charging air, comprising directing air through a mixer/charger, simultaneously mixing and electrically charging such air flowing through the mixer/charger, mixing said electrically charged air with ambient air, and distributing the air to the surrounding environment.

* * * * *